United States Patent [19]

Murakami et al.

[11] 4,074,062

[45] Feb. 14, 1978

[54] PROCESS FOR PRODUCING UNSATURATED CARBOXYLIC ACID ESTERS

[75] Inventors: Fumiki Murakami, Otake; Soichi Teshima, Yamaguchi; Toshihiko Yokoyama, Otake, all of Japan

[73] Assignee: Mitsubishi Rayon Company, Limited, Tokyo, Japan

[21] Appl. No.: 703,263

[22] Filed: July 7, 1976

[30] Foreign Application Priority Data

Aug. 21, 1975 Japan .............................. 50-101436
Aug. 21, 1975 Japan .............................. 50-101437
Mar. 12, 1976 Japan .............................. 51-26834

[51] Int. Cl.$^2$ ............................................ C07C 69/54
[52] U.S. Cl. .................................. 560/217; 560/204; 260/295 R; 260/293.88; 544/171
[58] Field of Search .................... 260/486 R, 485 R

[56] References Cited

U.S. PATENT DOCUMENTS

| 3,220,982 | 11/1965 | Advani ........................... 260/486 R |
| 3,329,826 | 7/1967 | Pine et al. ...................... 260/486 R |
| 3,442,935 | 5/1969 | Pine et al. ...................... 260/486 R |

FOREIGN PATENT DOCUMENTS

| 1,469,997 | 1/1967 | France ........................... 260/486 R |

*Primary Examiner*—Paul J. Killos
*Attorney, Agent, or Firm*—Oblon, Fisher, Spivak, McClelland & Maier

[57] ABSTRACT

An ester of an unsaturated carboxylic acid is prepared by an ester exchange process which comprises reacting a lower alkyl ester of an unsaturated, 3-4 carbon atom carboxylic acid with an alcohol different than the alcohol fragment of said lower alkyl ester over a catalyst selected from the group consisting of (1) metallic barium, barium compounds and mixtures thereof, (2) metallic thallium, thallium compounds or mixtures thereof, (3) metallic molybdenum, molybdenum compounds or mixtures thereof, and mixtures thereof by an ester exchange reaction.

17 Claims, No Drawings

PROCESS FOR PRODUCING UNSATURATED CARBOXYLIC ACID ESTERS

BACKGROUND OF THE INVENTION

Field of the Invention

Esters of unsaturated carboxylic acids can be produced by well known ester exchange reactions. In this type of reaction catalysts are generally used such as sulfuric acid and paratoluenesulfonic acid and alcoholates such as alkali metal alcoholates, aluminum alcoholates and titanium alcoholates. However, these catalysts have their drawbacks. For instance, when an acid catalyst such as sulfuric acid is used, the reaction rate is slow and the production of undesired polymer by-product increases. Furthermore, when a primary alcohol is used as a starting material, an ether by-product is produced. When a secondary alcohol is used as a starting material, a portion of the alcohol is dehydrated and an olefin is formed as a by-product. Other problems exist in that the ester exchange, the reaction will not proceed with some kinds of alcohols, and the reaction apparatus frequently corrodes.

On the other hand, when an alkali metal alcoholate such as sodium methylate is used as the catalyst, not only do such undesirable secondary reactions simultaneously occur such as the by-production of an additional reaction product, the by-production of an alkali metal salt and an anionic polymerization reaction, but also complicated procedures are necessary such as the continuous addition of catalyst to the reaction mixture as it loses its activity with the passage of time and the thorough prior dehydration of the catalyst because the catalyst loses its activity with time by reacting with water in the reaction system. Further, the catalyst must be washed with water and removed from the reaction mixture to prevent polymerization before the obtained product is separated from the reaction medium such as by distillation. This is a complicated process step. In addition the process necessitates the treatment of waste water from the reaction.

When aluminum alcoholate or titanium alcoholate is used as the catalyst, not only do the same drawbacks exist as when alkali metal alcoholates are used, but the catalysts lose activity with the passage of time and by the influence of water, but also the catalytic activity of these catalysts will diminish to a level less than the alkali metal alcoholate catalysts. Consequently, the amount of catalyst must be increased or the reaction time must be lengthened. Because of these problems with the conventional catalysts, a need continues to exist for an improved catalyst for ester exchange reactions which overcomes the deficiencies of the conventional catalysts.

SUMMARY OF THE INVENTION

Accordingly, one object of the invention is to provide a catalyst for the ester exchange reaction of carboxylic acid esters of improved activity.

Another object of the invention is to provide a method for conducting the ester exchange reaction of carboxylic acid esters over a catalyst of improved activity.

Briefly, these objects and other objects of the invention as will hereinafter become more readily apparent can be attained by a method for preparing an ester of an unsaturated carboxylic acid by an ester exchange process which comprises reacting a lower alkyl ester of an unsaturated, 3-4 carbon atom carboxylic acid with an alcohol different than the alcohol fragment of said lower alkyl ester over a catalyst selected from the group consisting of (1) metallic barium, barium compounds or mixtures thereof, (2) metallic thallium, thallium compounds or mixtures thereof, (3) metallic molybdenum, molybdenum compounds or mixtures thereof, and mixtures thereof by an ester exchange reaction.

DETAILED DESCRIPTION OF THE PREFERRED EMBODIMENTS

Suitable unsaturated carboxylic acid esters which can be used as starting materials in the present invention, include alkyl esters of such monocarboxylic acids as acrylic acid, methacrylic acid and crotonic acid, and alkyl esters of such dicarboxylic acids as fumaric acid and maleic acid. However, the alkyl radical of the ester is a lower alkyl radical than the alkyl radical in the starting material alcohol, and preferably a methyl or ethyl carboxylic acid ester is used. The alcohols which are used as a reactant in the present invention include all alcohols having boiling points higher than that of the alcohol produced by the ester exchange reaction. Suitable alcohols include alkanols, alkoxyalkanols, alkenoxyalkanols, alkenols, alkynols, alkylaminoalcohols, glycols, triols, polyhydric alcohols higher than triols, phenoxyalkanols, alkylphenoxyalkanols, cycloalkanols, alkylcycloalkanols, phenylalkanols, alkylphenylalkanols, alkylmorpholinoalkanols, alkylpiperidinoalkanols, pyridylalkanols, alkanol halides, cyanoalkanols and alkylthioalkanols. Particularly useful and preferable are alcohols containing not less than four carbon atoms. More specific examples of suitable alcohols include n-, i- and t-butanols, 2-ethylhexanol, laurylalcohol, stearylalcohol, cyclohexylalcohol, dimethylaminoethanol, diethylaminoethanol, glycidylalcohol, tetrahydrofurfurylalcohol, ethyleneglycol, triethyleneglycol, tetraethyleneglycol, 1, 3-butanediol, allylalcohol and trimethylolpropane. These alcohols can be used as they are without being dehydrated.

The catalyst of the present invention is composed of metallic barium and/or barium compounds. Suitable barium compounds include the oxides, chlorides, sulfides, hydroxides, inorganic acid salts, organic acid salts, phenolates and chelates of barium. More specifically, suitable catalyst materials include metallic barium, barium oxide, barium peroxide, barium hydroxide, barium nitrate, barium carbonate, barium sulfate, barium sulfite, barium nitrate, barium chromate, barium molybdate, barium selenite, barium phosphate, barium metaphosphate, barium permanganate, barium borate, barium chloride, barium bromate, barium fluoride, barium iodide, barium sulfide, barium thiocyanate, barium titanate, barium tungstate, barium acetate, barium formate, barium oxalate, barium stearate, barium acrylate and barium methacrylate. Among these specific materials, metallic barium, barium oxide (BaO) and barium hydroxide promote high reaction rates, and are preferred catalysts. When barium oxide is used as the catalyst, the occurence of secondary reactions is greatly diminished and is therefore preferred.

Another embodiment of the catalyst of the invention is the use of metallic thallium and/or thallium compounds. Besides metallic thallium, the catalyst can be formulated from such a wide range of thallium compounds as oxides, chlorides, inorganic acid salts, organic acid salts, hydroxides, sulfides, alcoholates, phenolates and chelate compounds of thallium. More specifically, suitable thallium compounds include thallium bromide, thallium carbonate, thallium chlorate, thallium chloride, thallium chromate, thallium cyanate, thallium fluoride, thallium hydroxide, thallium iodide, thallium nitrate, thallium monoxide, thallium trioxide (thallium sesquioxide), thallium perchlorate, thallium phosphate, thallium selenate, thallium sulfate, thallium sulfite, thallium sulfide, thallium vanadate, thallium formate, thallium acetate, thallium malonate, thallium oxalate, thallium (meth)acrylate, thallium methylate and thallium ethylate. Among these materials, metallic thallium, thallium monoxide ($Tl_2O$) and thallium trioxide ($Tl_2O_3$) promote high reaction rates and are particularly preferred.

Yet another embodiment of the catalyst of the invention is the use of metallic molybdenum and/or molybdenum compounds. Besides metallic molybdenum the catalyst can be formulated from a range of molybdenum oxides, halides, sulfides, inorganic acid salts, organic acid salts and chelate compounds of molybdenum. More specifically, suitable molybdenum compounds include molybdenum trioxide, molybdenum chloride, molybdenum bromide, molybdenum fluoride, molybdenum oxychloride, molybdenum oxybromide, molybdenum oxyfluoride, molybdenum phosphate, molybdenum sulfide, molybdic acid, phosphomolybdic acid, molybdenum benzoate, molybdenum hexacarbonyl, molybdenum dialkyldithiocarbonate, molybdenum oxalate and molybdenum acetylacetonate.

Among these materials, metallic molybdenum, molybdenum trioxide, molybdenum chloride, molybdenum acetylacetonate, molybdenum phosphate and molybdenum sulfide promote high reaction rates and are preferred catalysts. Most preferred are molybdenum trioxide and molybdenum acetylacetonate.

These above enumerated catalysts can be used singly or in mixtures.

In the present reaction, a solvent is normally used which forms an azeotropic mixture with the alcohol produced in the ester exchange reaction and which is inert to the reaction. Suitable solvents include hexane, benzene and cyclohexane.

Because polymerizable substances are handled in the present reaction, it is preferred to conduct the reaction in the presence of a polymerization inhibitor. Suitable polymerization inhibitors include hydroquinone, hydroquinone monomethyl ether, di-t-butylcatechol, phenothiazine, p-phenylenediamine and methylene blue.

In the present invention, the mole ratio of the alkyl ester of the unsaturated carboxylic acid to the alcohol is 1.0 to 10 : 1, preferably 1.1 to 5.0:1. Needless to say, any other ratio may be used, but there is no advantage in doing so from the viewpoint of economy.

All of the catlyst may be used from the first, or the catalyst may be added in increments over regular intervals or it may be continuously added to the reaction mixture. However, during normal operations, all of the catalyst is preferably present from the start of the reaction.

The amount of catalyst used can vary considerably. However, it is generally used in amounts of 0.0001 to 1.0 mole per mole of the starting material alcohol, preferably 0.001 to 0.5 mole.

The temperature usually employed for the ester exchange reaction ranges from 30° to 170° C, preferably 60° to 160° C. The reaction can also be conducted under a reduced pressure.

Having generally described the invention, a more complete understanding can be obtained by reference to certain specific examples, which are provided herein for purposes of illustration only and are not intended to be limiting unless otherwise specified.

In the examples and control examples, the unreacted starting materials and reaction products were quantitatively determined by gas chromatography. The conversion rate of the starting alcohol and the yield of the product ester were represented on the basis of the starting alcohol (ROH). That is to say, yield and conversion were calculated by formulas (1) and (2):

$$\text{(ROH) Conversion} = \frac{\text{Charge ROH (moles)} - \text{Unreacted ROH (moles)}}{\text{Charge ROH (moles)}} \times 100 \quad (1)$$

$$\text{Yield of Product Ester} = \frac{\text{Produced ester (moles)}}{\text{Charge ROH (moles)}} \times 100 \quad (2)$$

EXAMPLE 1

An 89.1g (1.0 mole) amount of dimethylaminoethyl alcohol, 300.4g (3.0moles) of methyl metacrylate, 120.4g (1.4 moles) of n-hexane, 3.84g (0.025 mole) of barium oxide (BaO) and 2g of phenothiazine were added to a one liter flask fitted with an agitator, thermometer and fractionating tower and were heated and agitated. An azeotropic mixture of n-hexane and methanol from the upper part (top) of the fractionating tower was obtained and was kept stationary in a decanter. The n-hexane layer which separated in the decantor was returned to the tower and the methanol layer was removed to continuously advance the reaction. The reaction was conducted for 3 hours while the temperature at the top of the tower was 56.0° to 59.8° C and the flask temperature was 86° to 93° C. The results of the experiment were that the conversion of dimethylaminoethyl alcohol was 98.2% and the yield of dimethylaminoethyl methacrylate was 95.8%. When this reaction solution was distilled, 146.1g of a fraction at 67 to 68° C under 10 mm. Hg were obtained. This fraction was established by gas chromatography to be dimethylaminoethyl methacrylate in a yield of 92.9%. By this experiment it was established that the reaction mixture could be directly distilled without the necessity of intermediate process steps such as washing the reaction medium with water.

EXAMPLE 2

The reaction was performed by adding 5.8g (0.0125 mole) of thallium trioxide ($Tl_2O_3$) to the reactants in the apparatus of Example 1 instead of the barium oxide. The results of the experiment were 98.8% conversion of dimethylaminoethyl alcohol and a 95.4% yield of dimethylaminoethyl methacrylate. When this ester was distilled in the same manner as in Example 1, it was recovered in a 93.4% yield.

EXAMPLE 3

A 148.2g (2.0 mole) amount of n-butanol, 400.5g (4.0 moles) of methyl methacrylate, 3.6g (0.025 mol) of molybdenum trioxide and 0.5g of hydroquinone monomethyl ether were added to the apparatus described in Example 1, and were heated and agitated. An azeotropic mixture of methanol and methyl methacrylate was obtained from the upper part of the fractionating tower. This mixture was removed at a reflux ratio of 2 to 10:1 to continuously advance the reaction. The reaction was conducted for four hours while the temperature at the top of the tower was 65° to 70° C and the flask temperature was 104° to 130° C. The reaction showed a 99.0% conversion of n-butanol and a 98.9% yield of n-butyl methacrylate.

When this reaction solution was directly distilled, 281g of a fraction of 93° to 94° C under 80 mm. Hg were obtained. This fraction was found by gas chromatography to be n-butyl methacrylate at a yield of 98.8%. It is clear that this reaction mixture can be distilled directly without the necessity of any intermediate process step such as water-washing.

EXAMPLES 4 to 49

Into the apparatus described in Example 1 were placed 1.0 mole of an alcohol shown in Table 1, 0.025 mol of a catalyst shown in Table 1 2.0 mols of methyl methacrylate per hydroxyl radical of the alcohol. A 0.5g amount of hydroquinone monomethyl ether was added as a polymerzation inhibitor to the reactants. In the case of catalysts of metallic barium, metallic thallium, barium compounds and thallium compounds, 1.4 mols of n-hexane were added to the reactants in the same manner described in Example 1 to promote the reaction. In the case of catalysts of metallic molybdenum and molybdenum compounds, the reaction was conducted in the same manner described in Example 3. The reaction results are shown in Table 1.

TABLE 1

| Example No. | Catalyst | Alcohol | Reaction time (hrs) | Alcohol conversion (%) | Ester Yield (%) |
|---|---|---|---|---|---|
| 4 | Metallic barium | N-butanol | 3.0 | 99.6 | 96.5 |
| 5 | | 2-ethylhexanol | 3.0 | 99.4 | 95.8 |
| 6 | | Dimethylaminoethanol | 3.0 | 99.4 | 95.9 |
| 7 | | Ethyleneglycol | 3.0 | 99.9 | 91.5 |
| 8 | Barium Oxide | N-butanol | 3.0 | 98.5 | 96.4 |
| 9 | | 2-ethylhexanol | 3.0 | 99.1 | 96.5 |
| 10 | | Lauryl alcohol | 3.0 | 98.2 | 95.5 |
| 11 | | Diethylaminoethanol | 3.0 | 98.6 | 94.5 |
| 12 | | Ethyleneglycol | 3.0 | 99.9 | 92.3 |
| 13 | | 1,3-butanediol | 3.0 | 99.9 | 91.8 |
| 14 | Barium hydroxide | N-butanol | 4.5 | 63.2 | 61.2 |
| 15 | | 2-ethylhexanol | 4.5 | 63.2 | 58.5 |
| 16 | | Dimethylaminoethanol | 4.5 | 69.1 | 61.8 |
| 17 | | Ethyleneglycol | 4.5 | 90.5 | 50.6 |
| 18 | Metallic thallium | N-butanol | 3.0 | 98.9 | 94.1 |
| 19 | | Dimethylaminoethanol | 3.0 | 99.6 | 96.0 |
| 20 | | Ethyleneglycol | 3.0 | 98.5 | 90.0 |
| 21 | Thallium monoxide | 2-ethylhexanol | 4.0 | 98.4 | 94.0 |
| 22 | | Dimethylaminoethanol | 3.0 | 99.2 | 94.2 |
| 23 | | 1,3-butanediol | 4.0 | 99.0 | 90.0 |
| 24 | Thallium trioxide | N-butanol | 5.0 | 98.3 | 95.0 |
| 25 | | 2-ethylhexanol | 6.5 | 98.8 | 94.9 |
| 26 | | Ethyleneglycol | 3.5 | 98.5 | 94.5 |
| 27 | Thallium acetate | Lauryl alcohol | 10.0 | 50.0 | 47.0 |
| 28 | | Dimethylaminoethanol | 7.0 | 72.2 | 68.6 |
| 29 | | Ethyleneglycol | 10.0 | 55.0 | 30.0 |
| 30 | Metallic molybdenum | 2-ethylhexanol | 4.0 | 99.0 | 98.5 |
| 31 | | Cyclohexanol | 4.0 | 98.8 | 98.5 |
| 32 | | Ethyleneglycol | 8.0 | 98.1 | 8.5 |
| 33 | Molybdenum trioxide | 2-ethylhexanol | 5.0 | 99.0 | 98.9 |
| 34 | | Lauryl alcohol | 6.5 | 98.5 | 98.4 |
| 35 | | Cyclohexanol | 6.0 | 98.5 | 98.4 |
| 36 | | Ethyleneglycol | 10.0 | 60.0 | 50.9 |
| 37 | | 1,3-butanediol | 10.0 | 50.0 | 40.9 |
| 38 | Molybdenum pentachloride | N-butanol | 2.0 | 99.6 | 98.9 |
| 39 | | Ethyleneglycol | 3.0 | 99.1 | 90.5 |
| 40 | Molybdenum acetylacetate | 2-ethylhexanol | 3.5 | 99.0 | 98.7 |
| 41 | | Ethyleneglycol | 4.0 | 99.2 | 90.6 |
| 42 | Phosphomolybdic acid | N-butanol | 5.5 | 98.7 | 98.6 |

TABLE 1-continued

| Example No. | Catalyst | Alcohol | Reaction time (hrs) | Alcohol conversion (%) | Ester Yield (%) |
|---|---|---|---|---|---|
| 43 | BaO—Tl₂O₃ | 2-ethylhexanol | 3.0 | 99.0 | 96.5 |
| 44 | BaO—Tl₂O₃ | Dimethylaminoethanol | 3.0 | 98.8 | 95.4 |
| 45 | BaO—MoO₃ | N-butanol | 3.0 | 98.5 | 97.0 |
| 46 | BaO—MoO₃ | Dimethylaminoethanol | 3.0 | 98.2 | 95.8 |
| 47 | Tl₂O₃—MoO₃ | 2-ethylhexanol | 4.0 | 98.8 | 96.0 |
| 48 | Tl₂O₃—MoO₃ | Dimethylaminoethanol | 3.0 | 98.5 | 95.2 |
| 49 | BaO—Tl₂O₃—MoO₃ | Dimethylaminoethanol | 3.0 | 99.0 | 95.5 |

EXAMPLES 50 to 58

Into the apparatus described in Example 1 were placed 2.0 mols of n-butanol, 4.0 mols of a starting material ester shown in Table 2, 0.025 mol of a catalyst shown in Table 2 and 0.5g of hydroquinonemonomethyl ether as a polymerization inhibitor to conduct a reaction in the same manner described in Example 3. The results are shown in Table 2.

TABLE 2

| Ex. No. | Starting Material ester | Catalyst | Reaction Time (hrs.) | Alcohol Conversion (%) | Ester Yield (%) |
|---|---|---|---|---|---|
| 50 | Methylacrylate | BaO | 3.0 | 99.1 | 95.2 |
| 51 | | Tl₂O₃ | 4.0 | 98.9 | 94.4 |
| 52 | | MoO₃ | 4.0 | 98.7 | 98.5 |
| 53 | Methyl crotonate | BaO | 3.0 | 98.4 | 95.0 |
| 54 | | Tl₂O₃ | 4.0 | 99.0 | 94.0 |
| 55 | | MoO₃ | 4.0 | 98.5 | 98.4 |
| 56 | Dimethyl furmarate | BaO | 3.0 | 99.0 | 92.0 |
| 57 | | Tl₂O₃ | 4.0 | 99.1 | 91.1 |
| 58 | | MoO₃ | 4.0 | 99.0 | 96.5 |

CONTROL EXPERIMENT 1

A 148.2g (2.0 mols) amount of n-butanol, 400.5g (4.0 mols) of methylmethacrylate, 0.5g of hydroquinonemonomethyl ether and 2.45g (0.025 mol) of concentrated sulfuric acid were added to a flask to conduct a reaction in the same manner described in Example 1. The reaction was carried out for 6 hours. The reaction results obtained were an 89.9% conversion of n-butanol and an 88.2% yield of n-butyl methacrylate. However, it was found by gas chromatography that a high boiling point by-product was present and 0.004 mol of methacrylic acid (2740 ppm. on n-butyl methacrylate) was produced as a by-product.

When this reaction solution was directly distilled in the same manner described in Example 1, the methylmethacrylate fraction polymerized when the distillation was finished and butylmethacrylate could not be recovered. Further, after the reaction was finished, when the reaction solution was washed twice with 50g of 10% caustic soda water and was then distilled in the same manner described in Example 1, 242g of a butyl methacrylate fraction were obtained. Therefore, the yield of ester product was only 85.0%.

CONTROL EXPERIMENT 2

A 74.1g (0.1 mole) amount of n-butyl alcohol, 200.2g (2.0 mols) of methyl methacrylate, 187g (2.18 mols) of n-hexane and 0.17 g of hydroquinonemonomethyl ether were added to the apparatus described in Example 1 and were heated and agitated under full reflux to remove water from the reaction system. The amount of water obtained in the reaction solution was 0.001 mol. To the reaction solution was added 0.0035 mol of sodium methylate as a catalyst and the solution was heated and agitated. An azeotropic mixture was n-hexane and methanol fom the upper part (top) of the fractionating tower was obtained and was kept stationary in a decanter. The n-hexane layer which separated was returned to the tower and the methanol layer was removed continuously to advance the reaction. Meanwhile, the temperature at the top of the tower was 56° to 59.8° C and the flask temperature was 83° to 90° C. The results of the experiment were a 98.8% conversion of n-butyl alcohol and a 95.1% yield of n-butyl methacrylate. However, it was found bu gas chromatography that an additive of methylmethacrylate was produced as a by-product as well as a polymer. As soon as this reaction solution was distilled, it polymerized.

It was also found that if the reaction was conducted without a dehydrating operation, it soon stopped. Even when the reaction was conducted for 6 hours, the conversion of n-butyl alcohol was only 34.2% and the yield of n-butylmethacrylate wa only 32.5%.

The advantages of the ester exchange process of the present invention over the conventional process are that the reaction velocity is high, there is no adverse influence by the production of water, the treatment of the catalyst after the reaction is easy, the secondary reactions are few and very little methacrylic acid is produced as a by-product. These are substantial industrial advantages.

Having now fully described this invention, it will be apparent to one of ordinary skill in the art that many changes and modifications can be made thereto without departing from the spirit or scope of the invention as set forth herein.

What is claimed as new and intended to be secured by Letters Patent is:

1. An ester exchange process which comprises:
  preparing an ester of unsaturated carboxylic acid by reacting a lower alkyl ester of an unsaturated, 3-4 carbon atom carboxylic acid with an alcohol different than the alcohol fragment of said lower alkyl ester over a catalyst selected from the group consisting of
    1. metallic barium, barium compounds or mixtures thereof;
    2. metallic thallium, thallium compounds or mixtures thereof;
    3. metallic molybdenum, molybdenum compounds or mixtures thereof, and mixtures thereof by an ester exchange reaction.

2. The ester exchange process of claim 1, wherein said lower alkyl ester is a methyl or ethyl ester and said alcohol contains not less than four carbon atoms.

3. The ester exchange process of claim 1, wherein said catalyst is selected from the group consisting of barium, barium compounds and mixtures thereof.

4. The ester exchange process of claim 3, wherein said catalyst is selected from the group consisting of metallic barium, barium oxide and barium hydroxide.

5. The ester exchange process of claim 3, wherein said barium compound is barium oxide.

6. The ester exchange process of claim 1, wherein said catalyst is selected from the group consisting of thallium compounds and mixtures thereof.

7. The ester exchange process of claim 6, wherein said catalyst is selected from the group consisting of metallic thallium, thallium monoxide, and thallium trioxide.

8. The ester exchange process of claim 7, wherein said catalyst is thallium monoxide.

9. The ester exchange process of claim 7, wherein said catalyst is thallium trioxide.

10. The ester exchange process of claim 1, wherein said catalyst is selected from the group consisting of metallic molybdenum, molybdenum compounds and mixtures thereof.

11. The ester exchange process of claim 10, wherein said catalyst is selected from the group consisting of metallic molybdenum, molybdenum trioxide, molybdenum chloride, molybdenum acetylacetonate, molybdenum phosphate and molybdenum sulfide.

12. The ester exchange process of claim 11, wherein said catalyst is molybdenum trioxide.

13. The ester exchange process of claim 10, wherein said molybdenum compound is molybdenum acetylacetonate.

14. The ester exchange process of claim 11, wherein said catalyst is molybdenum chloride.

15. The ester exchange process of claim 1, wherein the amount of the catalyst used relative to said alcohol is a mole ratio of 0.001 to 0.5:1.

16. The ester exchange process of claim 1, wherein the reaction temperature is 30 to 170° C.

17. The ester exchange process of claim 1, wherein the exchange reaction is conducted in a solvent which forms an azeotropic mixture with the alcohol produced in the ester exchange reaction and which is inert to the reaction.

* * * * *